United States Patent
Luebke et al.

(10) Patent No.: US 10,001,448 B2
(45) Date of Patent: Jun. 19, 2018

(54) GAS SENSOR

(71) Applicant: King Abdullah University of Science and Technology, Thuwal (SA)

(72) Inventors: Ryan Luebke, Thuwal (SA); Mohamed Eddaoudi, Thuwal (SA); Hesham Omran, Thuwal (SA); Youssef Belmabkhout, Thuwal (SA); Osama Shekhah, Thuwal (SA); Khaled N. Salama, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 554 days.

(21) Appl. No.: 14/375,665

(22) PCT Filed: Jan. 30, 2013

(86) PCT No.: PCT/US2013/023764
§ 371 (c)(1),
(2) Date: Jul. 30, 2014

(87) PCT Pub. No.: WO2013/137985
PCT Pub. Date: Sep. 19, 2013

(65) Prior Publication Data
US 2015/0020577 A1 Jan. 22, 2015

Related U.S. Application Data

(60) Provisional application No. 61/592,547, filed on Jan. 30, 2012.

(51) Int. Cl.
*G01N 27/02* (2006.01)
*G01N 33/00* (2006.01)
(Continued)

(52) U.S. Cl.
CPC .......... *G01N 27/02* (2013.01); *G01N 27/041* (2013.01); *G01N 27/12* (2013.01);
(Continued)

(58) Field of Classification Search
CPC . G01N 27/12; G01N 33/0027; G01N 33/0031
See application file for complete search history.

(56) References Cited

U.S. PATENT DOCUMENTS 4,703,646 A * 11/1987 Muller ............... G01N 27/4141
338/34
6,111,280 A 8/2000 Gardner et al.
(Continued)

FOREIGN PATENT DOCUMENTS

DE 10 2009 047201 A1 6/2011
EP 2087916 A1 8/2009
(Continued)

OTHER PUBLICATIONS

International Search Report and Written Opinion of the International Searching Authority for PCT/US2013/023764, dated Jun. 28, 2013 (Jun. 28, 2013), entire document.
(Continued)

*Primary Examiner* — Paul West
(74) *Attorney, Agent, or Firm* — Billion & Armitage; Benjamin C. Armitage (57) ABSTRACT

A gas sensor using a metal organic framework material can be fully integrated with related circuitry on a single substrate. In an on-chip application, the gas sensor can result in an area-efficient fully integrated gas sensor solution. In one aspect, a gas sensor can include a first gas sensing region including a first pair of electrodes, and a first gas sensitive material proximate to the first pair of electrodes, wherein the first gas sensitive material includes a first metal organic framework material.

21 Claims, 8 Drawing Sheets

(51) Int. Cl.
  *G01N 27/04* (2006.01)
  *G01N 27/12* (2006.01)
(52) U.S. Cl.
  CPC ..... *G01N 33/0027* (2013.01); *G01N 33/0031* (2013.01); *Y10T 29/49117* (2015.01)

(56) References Cited

U.S. PATENT DOCUMENTS

| | | | |
|---|---|---|---|
| 6,341,629 B1* | 1/2002 | Clark | G01N 33/2829 141/1 |
| 2007/0202012 A1* | 8/2007 | Steichen | G01N 33/0031 422/98 |
| 2008/0220535 A1* | 9/2008 | LeBoeuf | G01N 27/305 436/164 |
| 2010/0132547 A1 | 6/2010 | Masel et al. | |
| 2011/0077447 A1 | 3/2011 | Groothuis et al. | |
| 2011/0174799 A1* | 7/2011 | Ali | H05B 3/267 219/446.1 |
| 2012/0116683 A1* | 5/2012 | Potyrailo | G01N 27/02 702/19 |

FOREIGN PATENT DOCUMENTS

| | | |
|---|---|---|
| WO | 2010078337 A1 | 7/2010 |
| WO | 2011136440 A1 | 11/2011 |

OTHER PUBLICATIONS

Achmann et al., "Metal-organic frameworks for sensing applications in the gas phase," Sensors (2009) 9: 1574-1589. XP055033423.
Baca et al., "Rapid detection of ebola virus with a reagent-free, point-of-care biosensor," Sensors (2015) 15: 8605-8614.
Kreno et al., "Metal-organic framework materials as chemical sensors," Chem. Rev. (2012) 112: 1105-1125. XP055208158.
Pohle et al., "Metal organic frameworks as promising high surface area material for work function gas sensors," Procedia Engineering (2011) 25: 108-111. XP055033390.
Yeom et al., "Enhanced toxic gas detection using a mems preconcentrator coated with the metal organic framework absorber," MEMS (2008): 232-235. XP031210725.
Extended European Search Report for corresponding EP Application No. 13761034.1 dated Aug. 25, 2015.
"Examination Report", Gulf Cooperation Council Patent Application No. 2013-23444, dated Jun. 29, 2016, 4 pages.
Allendorf, et al., "A Roadmap to Implementing Metal-Organic Frameworks in Electronic Devices: Challenges and Critical Directions", Chem. Eur. J., 2011, 17, 11372-11388.
Asad, et al., "High sensitive and selective flexible H2S gas sensors based on Cunanoparticle decorated SWCNTs", Sensors and Actuators B 210 (2015) 1-8.
Asad, et al., "Highly sensitive wireless H2S gas sensors at room temperature basedon CuO-SWCNT hybrid nanomaterials", Sensors and Actuators B 231 (2016) 474-483.
Choi, et al., "Facile Au catalyst loading on the inner shell of hollow SnO2 spheres using Au-decorated block copolymer sphere templates and their selective H2S sensing characteristics", Nanoscale, 2014, 6, 11898-11903.
Choi, et al., "Highly Efficient Electronic Sensitization of Non-oxidized Graphene Flakes on Controlled Pore-loaded WO3 Nanofibers for Selective Detection ofH2S Molecules", Scientific Reports, 5, 8067, Jan. 28, 2015, 1-9.
Crowley, et al., "Fabrication of Polyaniline-Based Gas Sensors Using Piezoelectric Inkjet and Screen Printing for the Detection of Hydrogen Sulfide", IEEE Sensors Journal, vol. 10, No. 9, Sep. 2010, 1419-1426.
Cui, et al., "Resonant tunneling modulation in quasi-2D Cu2O/SnO2 p-n horizontalmulti-layer heterostructure for room temperature H2S sensor application", Scientific Reports, 3, 1250, Feb. 13, 2013, 1-8.
Eddaoudi, et al., "Systematic Design of Pore Size and Functionality in Isoreticular MOFs and Their Application in Methane Storage", Science, vol. 295, Jan. 18, 2002, 469-472.
Fedder, et al., "Technologies for Cofabricating MEMS and Electronics", Proceedings of the IEEE, vol. 96, No. 2, pp. 306-322, 2008.
Fu, et al., "High response and selectivity of a Cu—ZnO nanowire nanogenerator as a self-powered/ active H2S sensor", Phys. Chem. Chem. Phys., 2015, 17, 2121-2126.
Gardner, et al., "CMOS interfacing for integrated gas sensors: A review.", IEEE Sensors Journal, vol. 10, No. 12, pp. 1833-1848, 2010.
Ghafar-Zadeh, et al., "CMOS capacitive sensors for lab-on-chip applications: A multidisciplinary approach", Springer, 2010.
Girija, et al., "Highly selective H2S gas sensor based on Cu-doped ZnO nanocrystalline films deposited by RF magnetron sputtering of powder target", Journal of Alloys and Compounds 684 (2016) 15-20.
Glass, "A Reviwe of the Health Effects of Hydrogen Sulphide Exposure", Ann. Occup. Hyg., vol. 34, No. 3, pp. 323-327, 1990.
Goldoni, et al., "Sensing gases with carbon nanotubes: A review of the actual situation", Journal of Physics Condensed Matter, vol. 22, No. 1, 2010.
Grover, "Interdigitated Array Electrode Sensors: Their Design, Efficiency, and Applications", University of Tennessee Honors Thesis Projects, May 10, 1999, 62 pages.
Hagleitner, et al., "Smart single-chip gas sensor microsystem", Nature, 414, Nov. 15, 2001, 293-296.
Hazardous Substances Databank, "Hydrogen sulfide", National Library of Medicine, Bethesda, MD, USA, 2011, <https://toxnet.nlm.nih.gov/cgi-bin/sis/search/a?dbs+hsdb:@term+@DOCNO+576, accessed Feb. 13, 2017>.
Hierlemann, et al., "CMOS-based chemical microsensors", Analyst, 2003, 128, 15-28.
Joo, et al., "Chemical Sensors with Integrated Electronics", Chemical Reviews, 2008, 108, 2, 638-651.
Kaur, et al., "Room-temperature H2S gas sensing at ppb level by single crystal In2O3 whiskers", Sensors and Actuators B 133 (2008) 456-461.
Kim, et al., "Characterization of malodorous sulfur compounds in landfill gas", Atmospheric Environment 39 (2005) 1103-1112.
Kim, et al., "The emission characteristics and the related malodor intensities of gaseous reduced sulfur compounds (RSC) in a large industrial complex", Atmospheric Environment 40 (2006) 4478-4490.
Li, et al., "Resistive gas sensors based on colloidal quantum dot (CQD) solids forhydrogen sulfide detection", Sensors and Actuators B 217 (2015) 198-201.
Ma, et al., "a-Fe2O3 nanochains: ammonium acetate-based ionothermal synthesis and ultrasensitive sensors for low-ppm-level H2S gas", Nanoscale, 2013, 5, 895-898.
Ma, et al., "Room temperature ppb level H2S detection of a single Sb-doped SnO2nanoribbon device", Sensors and Actuators B 216 (2015) 72-79.
McKinlay, et al., "BioMOFs: Metal-Organic Frameworks for Biological and Medical Applications", Angew. Chem. Int. Ed., 2010, 49, 6260-6266.
Meek, et al., "Metal-Organic Frameworks: A Rapidly Growing Class of Versatile Nanoporous Materials", Adv. Mater. 2011, 23, 249-267.
OSHA, Occupational Safety and Health Administration, Fact sheet of Hydrogen sulfide (H2S), DSG Oct. 2005 <http://www.osha.-gov/OshDoc/data_Hurricane_Facts/hydrogen_sulfide_fact.pdf>.
Potyrailo, et al., "Materials and Transducers Toward Selective Wireless Gas Sensing", Chem Rev., Nov. 9, 2011, 111(11), 7315-7354.
Ratinac, et al., "Toward ubiquitous environmental gas sensors—Capitalizing on the promise of graphene", Environmental Science and Technology, vol. 44, No. 4, pp. 1167-1176, 2010.
Rheaume, et al., "A review of recent progress in sensing of gas concentration by impedance change", Ionics, vol. 17, No. 2, pp. 99-108, 2011.

(56) References Cited

OTHER PUBLICATIONS

Sapsanis, et al., "Insights on Capacitive Interdigitated Electrodes Coated with MOF Thin Films: Humidity and VOCs Sensing as a Case Study", Sensors 2015, 15, 18153-18166.
Sarfraz, et al., "Printed hydrogen sulfide gas sensor on paper substrate based on polyaniline composite", Thin Solid Films 534 (2013) 621-628.
Shekhah, et al., "MOF thin films: existing and future applications", Chem. Soc. Rev. 2011, 40, 1081-1106.
Wales, et al., "Gas sensing using porous materials for automotive applications", Chem. Soc. Rev., 2015, 44, 4290-4321.
Wu, et al., "Stably dispersed carbon nanotubes covalently bonded to phthalocyanine cobalt(II) for ppb-level H2S sensing at room temperature", J. Mater. Chem. A, 2016, 4, 1096-1104.
Xue, et al., "Tunable Rare Earth fcu-MOF Platform: Access to Adsorption Kinetics Driven Gas/Vapor Separations via Pore Size Contraction", J. Am. Chem. Soc., 2015, 137, 5034-5040.
Yu, et al., "Low concentration H2S detection of CdO-decorated hierarchicallymesoporous NiO nanofilm with wrinkle structure", Sensors and Actuators B 230 (2016) 706-713.
Zhang, et al., "Chemical and biological technologies for hydrogen sulfide emission control in sewer systems: A review", Water Research 42 ( 2008 ) 1-12.

\* cited by examiner

GAS SENSOR

CLAIM FOR PRIORITY

This application claims priority under 35 USC 371 to International Application No. PCT/US2013/023764, filed Jan. 30, 2013, which claims priority to U.S. Provisional Patent Application No. 61/592,547, filed Jan. 30, 2012, each of which is hereby incorporated by reference in its entirety.

TECHNICAL FIELD

This invention relates to an integrated gas sensor.

BACKGROUND

Over the past decades, sensor microsystems developed from simple transducers to a complete microsystem can include signal conditioning, analog-to-digital conversion, intelligence, and wireless link. Integrating sensors with electronic circuitry can offer several advantages, e.g., reduced size, weight, and cost, improved signal transduction, lower power consumption, and improved immunity to external noise sources.

Gas sensors find numerous industrial, medical, scientific, and military applications. One important application can include monitoring of toxic gases in oil and petrochemical industries. Another application can be building wireless gas sensor networks for environmental monitoring over large areas. Although the topic of gas sensing is relatively old, recent reviews show that the selectivity, dynamic range, and integration level of available gas sensors continue to fall short of the requirements of different applications.

SUMMARY

A gas sensor using a metal organic framework material can be fully integrated with related circuitry on a single substrate. In an on-chip application, the gas sensor can result in an area-efficient fully integrated gas sensor solution.

In one aspect, a gas sensor can include a first gas sensing region including a first pair of electrodes, and a first gas sensitive material proximate to the first pair of electrodes, wherein the first gas sensitive material includes a first metal organic framework material.

The gas sensor can further include a monitor module electrically connected to the first pair of electrodes and configured to monitor at least one electronic property of the first gas sensitive material. The electronic property of the first gas sensitive material monitored by the monitor module includes one or more of impedance, resistance, or capacitance.

In another aspect, a chip can include the gas sensor described herein.

In another aspect, an on-chip microsystem for gas sensing can include the gas sensor described herein.

In another aspect, a method of making a gas sensor can include forming a first pair of electrodes on a substrate, and forming a first gas sensitive metal organic framework material proximate to the first pair of electrodes.

The method can further include forming a monitor module on the substrate to monitor at least one electronic property of the first gas sensitive metal organic framework material. The method can include forming a second pair of electrodes on the substrate.

In another aspect, a gas sensor system can include a substrate, and a plurality of gas sensor described herein on the substrate.

In another aspect, a method of monitoring a gas concentration includes exposing a gas sensor region to a detectable gas; monitoring at least one electronic property of a gas sensitive material including a metal organic framework material; and correlating the electronic property of the gas sensitive material with the presence of the detectable gas The first pair of electrodes can be interdigitated. Both of the first pair of electrodes and the monitor module are on a single substrate.

A material is proximate to another structure of the device if it is nearby that structure in a manner that allows the device to function. In some embodiments, the proximate material is in contact with the other structure of the device. In other embodiments, the proximate material is in contact with another material which is in contact with the other structure of the device. For example, the first gas sensitive material can be on top of the first pair of electrodes.

The gas sensor can further include a second gas sensing region including a second pair of electrodes, and a second gas sensitive material proximate to the second pair of electrodes. The second gas sensitive material can include a second metal organic framework material. The first and second pair of electrodes can be on the same substrate. The first and second pair of electrodes can have different compositions, different dimensions, or combinations thereof. The first and second metal organic framework materials can have different compositions, different dimensions, or combinations thereof. The gas sensor can include a plurality of gas sensing regions, such as, 2, 3, 4 or more regions in a single gas sensor.

The gas sensor can include a passivation layer between the gas sensitive material and the electrodes. The gas sensor can include a filter layer proximate to the gas sensitive material for enhancing the selectivity of the gas sensor. The filter layer can include a metal organic framework.

The gas sensor can include a wireless communication module to transmit a measurement result of the monitor module. The gas sensor can be configured to receive power from a power unit. The power unit can include a battery. The power unit can include an energy harvesting device to collect energy from one or more of ambient energy sources, including solar energy, thermal energy, or radio frequency energy. In certain embodiments, the energy harvesting device can be a component of a microsystem including the gas sensor, for example, on the same chip.

Other aspects, embodiments, and features will be apparent from the following description, the drawings, and the claims.

DESCRIPTION OF DRAWINGS

FIGS. 2 A-C are diagrams illustrating gas sensors with different configurations.

FIGS. 4 A-B are diagrams illustrating the capacitance to voltage conversion circuits.

DETAILED DESCRIPTION

Integrated gas sensors can be fabricated with standard circuitry, including complementary metal oxide circuitry (CMOS). CMOS gas sensors are described, for example, in W. Gardner, P. K. Guha, F. Udrea & J. A. Covington, "CMOS interfacing for integrated gas sensors: A review," IEEE Sensors Journal, vol. 10, no. 12, pages 1833-1848, 2010, which is incorporated by reference in its entirety. Metal organic framework materials (MOFs) are crystalline materials composed of both inorganic and organic components in a porous networked structure. Metal organic framework materials exhibit exceptionally high specific surface area, in addition to tunable pore size and functionality, which make them attractive in many applications, including gas storage, gas separation, catalysis, drug delivery, light-emitting devices, and sensing. See, for example, Scott T. Meek, "Metal-Organic Frameworks: A Rapidly Growing Class of Versatile Nanoporous Materials," Advanced Materials. 2011; 23(2):249-267; Mark D. Allendorf, Adam Schwartzberg, Vitalie Stavila & A. Alec Talin, "A Roadmap to Implementing Metal-Organic Frameworks in Electronic Devices: Challenges and Critical Directions." Chemistry—A European Journal, vol. 17, no. 41, pages 11372-11388, 2011; and O. Shekhah, J. Liu, R. A. Fischer and Ch. Wöll, "MOF thin films: existing and future applications" Chem. Soc. Rev., 2011, 40, 1081-1106, each of which is incorporated by reference in its entirety. An integrated sensor using metal organic framework material capitalizes on the unique properties of MOFs that allow them to be integrated in gas sensor microsystems. The sensor microsystem can be implemented in a lab-on-chip (LoC) for environmental monitoring and assessment of manufacturing plant conditions, air quality, and air pollution. Examples of LoC structures can be found, for example, in Ebrahim Ghafar-Zadeh & Mohamad Sawan, "CMOS capacitive sensors for lab-on-chip applications: A multidisciplinary approach" Springer, 2010, which is incorporated by reference in its entirety.

The metal organic framework material can passivate an active layer of a gas sensor. Alternatively, the metal organic framework material can be selected to change in capacitance or resistance upon exposure to a gas to be detected. The properties of the metal organic framework material can be adjusted by design of the material. Due to the presence of inorganic and organic molecules in the metal organic framework material, the pore size and the chemical behavior of the metal organic framework material can be tuned to satisfy specific requirements, which make them more versatile than other porous inorganic materials Metal organic framework materials can serve as transducers by changing electronic, optical, or structural properties upon exposure to an analyte. Examples of transduction mechanisms include change in dielectric constant, change in luminescence signal, structural swelling, and mass change. These types of changes can be detected by various methodologies, including by monitoring capacitance or resistance of the material. The versatility of metal oxide framework materials due the ability to tune pore size and chemical functionality, in addition to their exceptionally high surface area, make these materials attractive for gas sensing applications. Gases for detection can include, but are not limited to, ammonia, carbon monoxide, carbon dioxide, volatile organic compounds (VOCs), water vapor, and light hydrocarbons.

Figure 1:
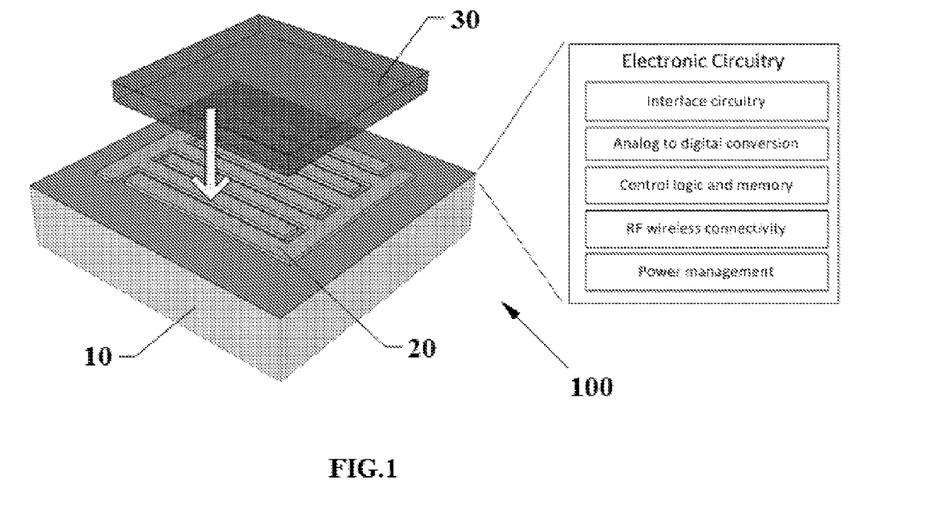
FIG. 1 is a diagram illustrating a gas sensor.

A schematic of an integrated gas sensor system is shown in FIG. 1. Gas sensor 100 includes two metal electrodes 20 and gas sensitive layer 30. Various electrode structures, such as interdigitated electrode structures, can be used. Electrodes can be built using the top metal layers of standard CMOS process with CMOS circuitry implemented on substrate 10.

Interface circuits to measure the change in resistance, capacitance or impedance (real and imaginary components) can be implemented on chip. The integrated microsystem can also include radiofrequency transceiver for wireless connectivity. Examples of sensors with wireless capability are described, for example, in Radislav A. Potyrailo, Cheryl Surman, Nandini Nagraj & Andrew Burns, "Materials and Transducers Toward Selective Wireless Gas Sensing," Chemical Reviews, vol. 111, no. 11, pages 7315-7354, 2011, which is incorporated by reference in its entirety. Control logic and memory can be used to store and process readings. The sensor or system can be powered by a battery or use energy harvesting techniques to collect energy from ambient energy sources, such as, for example, solar energy, thermal energy, or radiofrequency energy, or combinations thereof.

The metal organic framework materials can be used as the main functional element (gas sensitive layer 30) or as an auxiliary element. If used as the main functional element, the metal organic framework material is deposited or grown onto sensing electrodes 20 and the electric properties of the material is monitored upon exposure to the gas analyte. The electrical property being monitored can be the impedance (real and imaginary components), resistance, or capacitance of the sensing layer.

Most metal organic framework materials are dielectrics. In this case, the capacitance will be the property being monitored. The change in capacitance can be due to a change in dielectric constant or swelling of the gas sensitive layer upon exposure to a specific gas.

Figure 2:
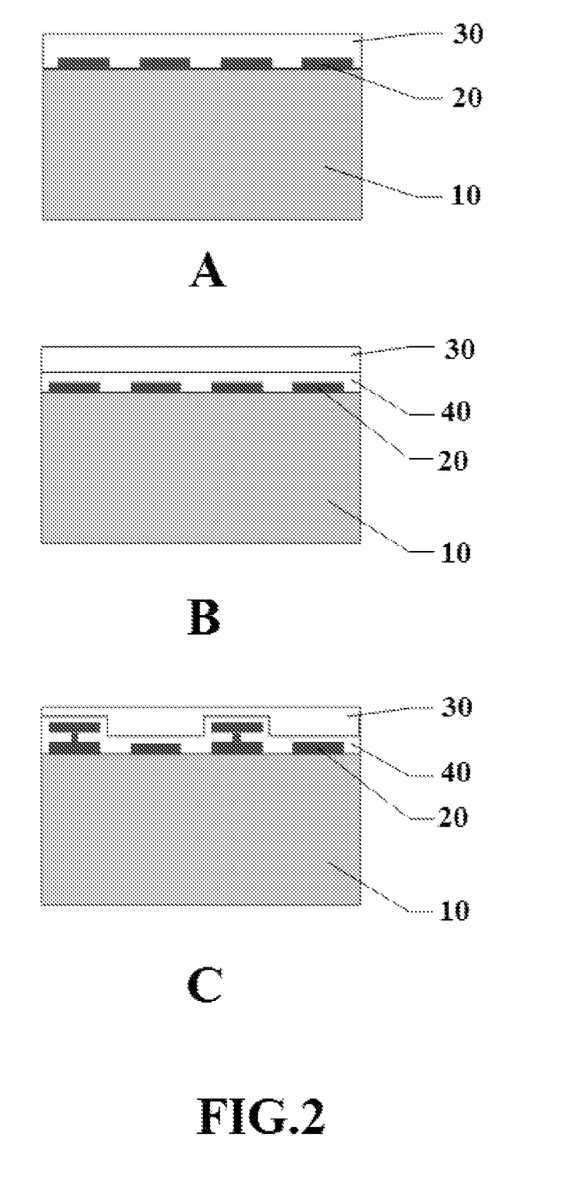

The deposition of metal organic framework materials as the gas sensitive material on the electrodes and the configuration of the gas sensor can take many forms as shown in FIG. 2. The bond pad etch can be used to remove any passivation layer and deposit the gas sensitive material 30 directly on top of metal electrodes 20 (A of FIG. 2). Interfacial layer 40 can be grown or deposited between electrodes 20 and gas sensitive material 30 as a passivation layer or adhesion layer (B of FIG. 2). In this case only the capacitance of gas sensitive material 30 can be monitored. Electrodes 20 can also have multilayer structure to increase the surface area, hence the total capacitance and the percentage of electric fields lines passing through gas sensitive material 30 (C of FIG. 2).

Figure 3:
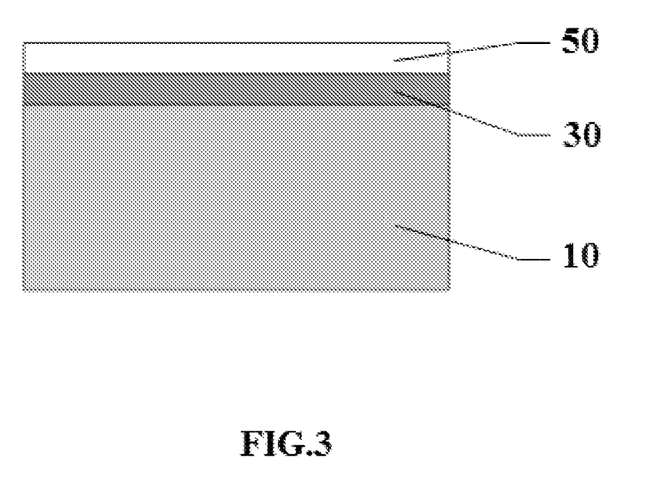
FIG. 3 is a diagram illustrating a gas sensor.

To be used as an auxiliary element of the gas sensor, metal organic framework material can act as a filter to enhance the selectivity of the gas sensor. As shown in FIG. 3, metal organic framework filter film 50 can be deposited on top of gas sensitive material 30, which can be another metal organic framework material or a different material.

Figure 4:
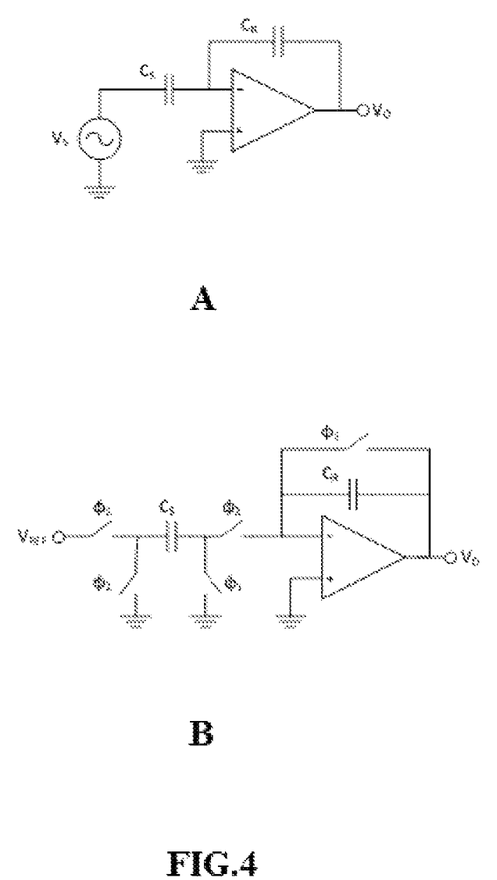

For measuring the small variations of resistance, a Wheatstone bridge can be used to convert the change in resistance into voltage. For capacitance to voltage conversion, continuous time or discrete time circuits can be used. Examples of continuous time circuit (A) and discrete time circuits (B) are shown in FIG. 4. Using fully differential circuits can yield improved performance. The voltage signal can be further digitized by on-chip analog-to-digital conversion circuitry.

Figure 5:
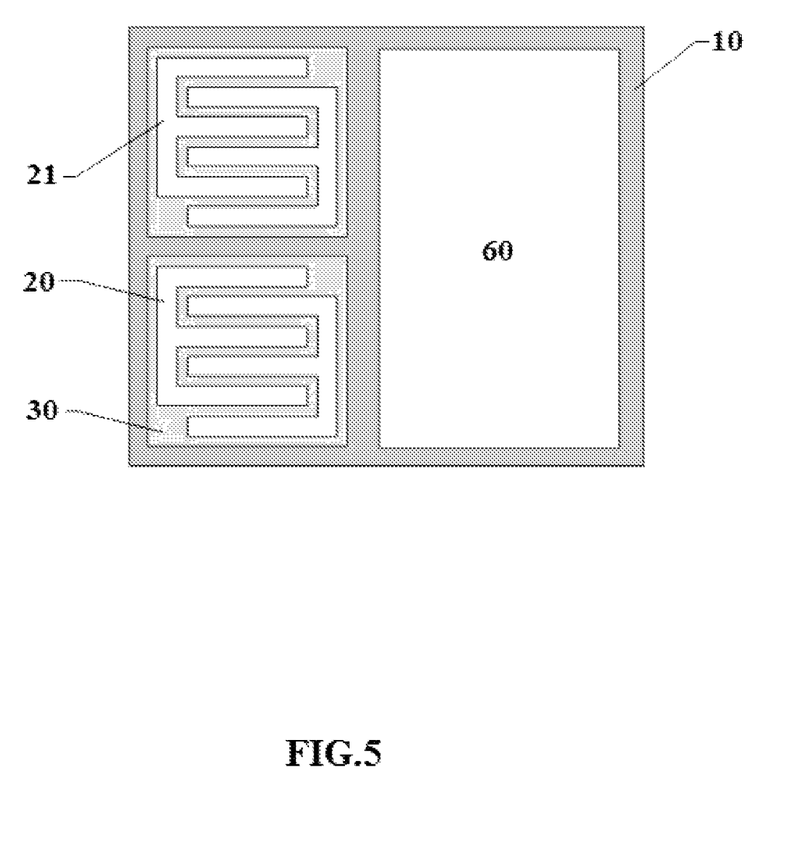
FIG. 5 is a diagram illustrating a gas sensor.

Using differential signal arrangement can yield improvement in performance. As shown in FIG. 5, reference electrodes 21 can be used in addition to sensing electrodes 20 in order to provide the differential change in impedance (real and imaginary components), capacitance or resistance. Reference electrodes 21 can be covered with passivation only, or can be covered with the same layers of sensing electrodes 20 but the packaging is arranged such that only sensing electrodes 20 are exposed to the gas analyte. Examples of using different signal arrangement are described, for example, in C. Hagleitner, D. Lange, A. Hierlemann, O. Brand & H. Baltes, "CMOS single-chip gas detection system comprising capacitive, calorimetric and mass-sensitive microsensors," Solid-State Circuits, IEEE Journal of, vol. 37, no. 12, pages 1867-1878, 2002, which is incorporated by reference in its entirety. Electronic circuit 60 can be fabricated on the same substrate.

Figure 6:
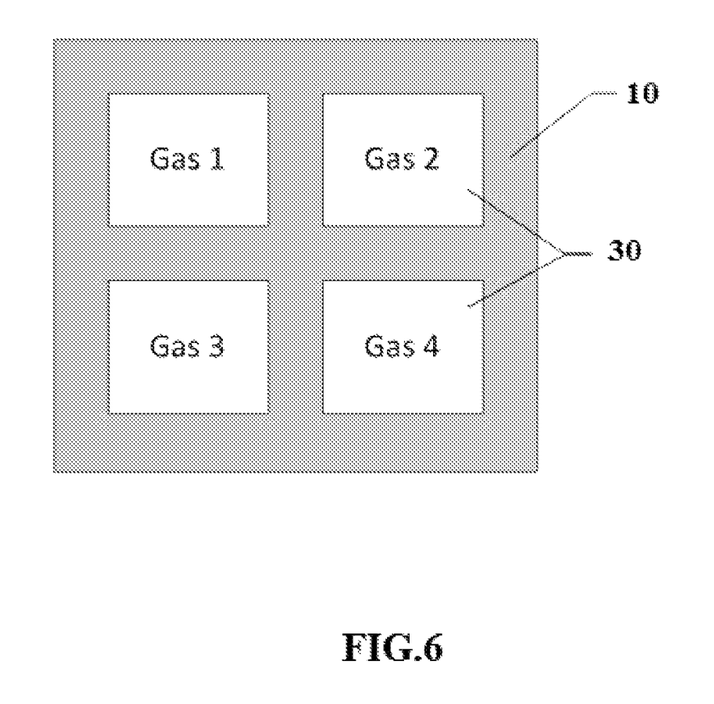
FIG. 6 is a diagram illustrating a gas sensor.
Figure 7:
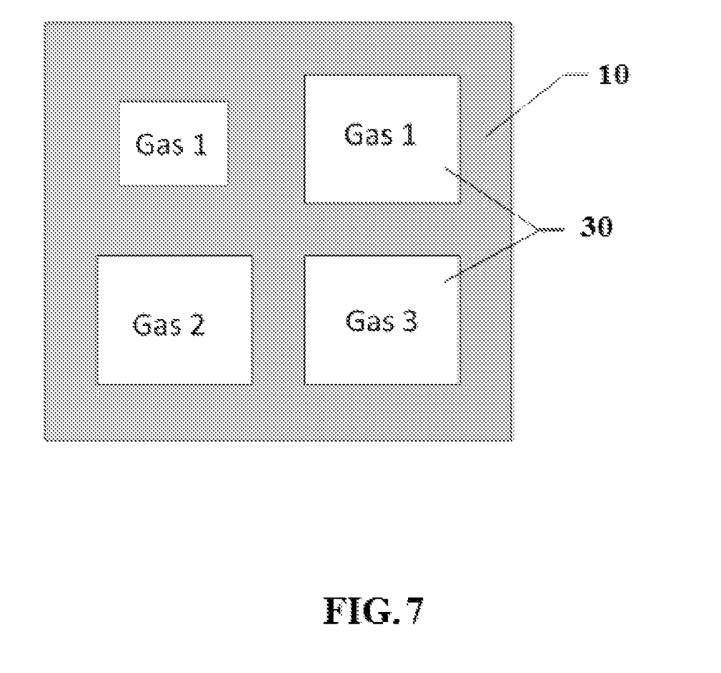
FIG. 7 is a diagram illustrating a gas sensor.

To sense different gases, several dies (each with a different metal organic framework material) can be integrated in a single package. Alternatively, different metal organic framework materials can be grown on the same die where each one is selective to a different gas, as shown in FIG. 6. Multiple metal organic framework materials can be also used to sense the same gas, but the units can have different physical parameters to have different dynamic range, sensitivity, etc., as shown in FIG. 7, and then sensor fusion techniques are used to produce an overall enhanced response. For example, metal organic framework materials can be different and have difference size or thickness.

In order to compensate for the effect of humidity, in addition to the gas sensitive material, another material can be used to sense humidity. A temperature sensor can be also integrated in order to compensate for the effect of temperature on the sensor response.

There are a few available methods to form metal organic framework materials on electrodes. Conditions are selected to achieve adhesion and stability for the gas sensor application. Metal organic framework materials can be formed from solvothermal mother solutions. In this approach, the substrate with sensing electrodes can be simply immersed into the solution during metal organic framework formation. Another method can be microwave-induced thermal deposition. To make a gas sensor with multiple layers of materials, liquid phase epitaxy (LPE) can be used. The substrate with sensing electrodes can be immersed into solutions of the reaction partners in a sequential, stepwise fashion to synthesize crystalline metal organic framework materials as thin films.

Figure 8:
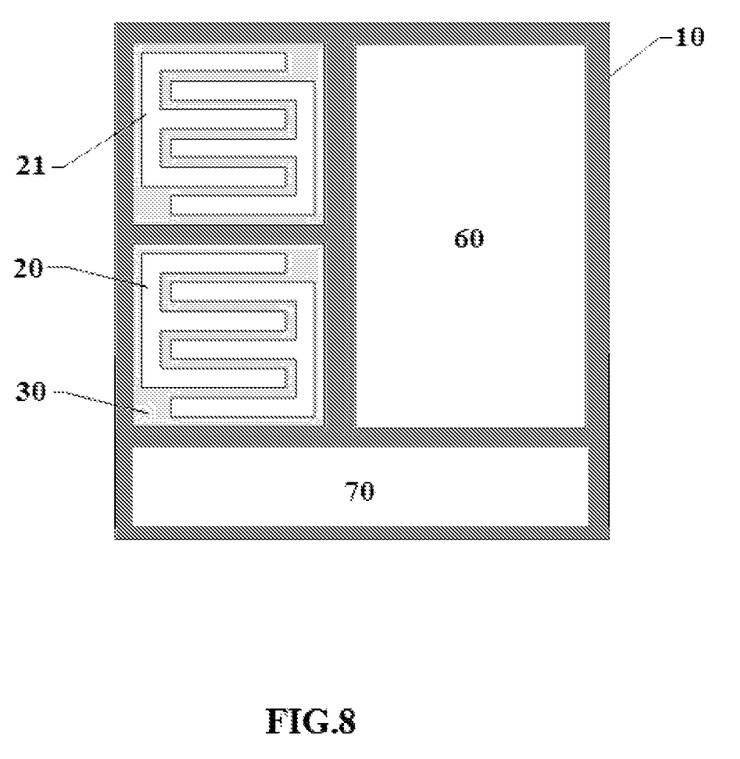
FIG. 8 is a diagram illustrating a gas sensor.

The sensor microsystem can include an integrated power unit and/or a power connecting interface. The sensor can be powered by a battery as an external or integrated component. The sensor can be self-powered using energy harvesting. As shown in FIG. 8, power unit 70 can be implemented on the same chip/substrate to supply power to electronic circuit 60. Power unit 70 can include a battery and/or an energy harvesting device to collect energy from one or more of ambient energy sources, including solar energy, thermal energy, or radio frequency energy.

A number of embodiments of the invention have been described. Nevertheless, it will be understood that various modifications may be made without departing from the spirit and scope of the invention. For example, although two capacitance to voltage conversion circuits are shown, the gas sensor can include any other suitable capacitance to voltage conversion circuit that can provide satisfied performance.

Other embodiments are within the scope of the following claims.

What is claimed is:

1. A gas sensor comprising:
    a first gas sensing region comprising
        a first pair of electrodes, wherein at least one of the first pair of electrodes is multilayered;
        a first gas sensitive material proximate to the first pair of electrodes, wherein the first gas sensitive material comprises a first metal organic framework material;
        an interfacial layer between the first pair of electrodes and the first gas sensitive material, wherein the interfacial layer is an adhesion layer or passivation layer; and
        a first filter layer on top of the first gas sensitive material for enhancing the selectivity of the gas sensor, wherein the first filter layer is a metal organic framework; and
    a monitor module electrically connected to the first pair of electrodes and configured to monitor at least one electrical property of the first gas sensitive material, wherein the electrical property includes capacitance.

2. The gas sensor of claim 1, wherein the first pair of electrodes are interdigitated.

3. The gas sensor of claim 1, wherein both of the first pair of electrodes and the monitor module are on a single substrate.

4. The gas sensor of claim 1, further comprising:
    a second gas sensing region proximate to the first gas sensing region comprising:
        a second pair of electrodes, and
        a second gas sensitive material proximate to the second pair of electrodes.

5. The gas sensor of claim 4, wherein the second gas sensitive material comprises a second metal organic framework material.

6. The gas sensor of claim 5, wherein the first metal organic framework material and second metal organic framework material are different compositions.

7. The gas sensor of claim 5, wherein the first metal organic framework material and second metal organic framework material are different dimensions.

8. The gas sensor of claim 4, wherein the first and second pair of electrodes are on a single substrate.

9. The gas sensor of claim 4, wherein the first and second pair of electrodes have different dimensions.

10. The gas sensor of claim 1, further comprising a wireless communication module to transmit a measurement result of the monitor module.

11. The gas sensor of claim 10, wherein the power unit comprises a battery.

12. The gas sensor of claim 10, wherein the power unit comprises an energy harvesting device to collect energy from one or more of ambient energy sources, including solar energy, thermal energy, or radio frequency energy.

13. The gas sensor of claim 1, wherein the gas sensor is configured to receive power from a power unit.

14. The gas sensor of claim 1, wherein the first gas sensitive material is on top of the first pair of electrodes.

15. A method of making a gas sensor, comprising:
    forming a first gas sensitive region on a substrate by placing a first gas sensitive metal organic framework material proximate to a first pair of electrodes, wherein the first pair of electrodes is multilayered;
    providing an interfacial layer between the first pair of electrodes and the first gas sensitive metal organic framework material, wherein the interfacial layer is an adhesion layer or passivation layer;
    depositing a filter layer on top of the first gas sensitive metal organic framework material for enhancing the selectivity of the gas sensor, wherein the first filter layer is a metal organic framework; and
    electrically connecting a monitor module to the first pair of electrodes for monitoring at least one electrical property of the first gas sensitive metal organic framework material, wherein the electrical property includes capacitance.

16. The method of claim 15, further comprising forming a second gas sensing region on the substrate.

17. The method of claim 15, further comprising forming a wireless communication module to transmit a measurement result of the monitor module.

18. The method of claim 15, wherein the first gas sensitive material is on top of the first pair of electrodes.

19. A gas sensor system, comprising:
  a substrate;
  a plurality of gas sensor units on the substrate, each unit comprising:
    a pair of electrodes, wherein at least one of the pair of electrodes is multilayered,
    a gas sensitive metal organic framework material proximate to the pair of electrodes;
    an interfacial layer between the pair of electrodes and the gas sensitive material, wherein the interfacial layer is an adhesion layer or passivation layer; and
    a filter layer on top of the gas sensitive material for enhancing the selectivity of the gas sensor, wherein the filter layer is a metal organic framework; and
  a monitor module electrically connected to each pair of electrodes and configured to monitor at least one electronic property of each gas sensitive metal organic framework material, wherein the electrical property includes capacitance.

20. The gas sensor system of claim 19, wherein each gas sensor unit includes a different gas sensitive metal organic framework material.

21. The gas sensor system of claim 19, further comprising a wireless communication module to transmit a measurement result of the monitor module.

* * * * *